(12) United States Patent
Wieloch et al.

US011033545B2

(10) Patent No.: US 11,033,545 B2
(45) Date of Patent: Jun. 15, 2021

(54) NEGATIVE ALLOSTERIC MODULATORS OF MGLUR5 FOR USE IN THE TREATMENT OF MATURE BRAIN DAMAGES

(71) Applicant: Sinntaxis AB

(72) Inventors: Tadeusz Wieloch, Lund (SE); Carin Sjölund, Malmo (SE); Kerstin Beirup, Lund (SE); Karsten Ruscher, Lund (SE); Roger Olsson, Bunkeflostrand (SE)

(73) Assignee: Sinntaxis AB, Lund (SE)

( * ) Notice: Subject to any disclaimer, the term of this patent is extended or adjusted under 35 U.S.C. 154(b) by 0 days.

(21) Appl. No.: 16/088,137

(22) PCT Filed: Mar. 30, 2016

(86) PCT No.: PCT/SE2016/050264
§ 371 (c)(1),
(2) Date: Sep. 25, 2018

(87) PCT Pub. No.: WO2017/171594
PCT Pub. Date: Oct. 5, 2017

(65) Prior Publication Data
US 2019/0365753 A1    Dec. 5, 2019

(51) Int. Cl.
*A61K 31/506* (2006.01)
*A61P 25/28* (2006.01)
*A61K 31/404* (2006.01)
*A61K 31/4168* (2006.01)
*A61K 31/4365* (2006.01)
*A61K 31/437* (2006.01)
*A61K 31/4439* (2006.01)

(52) U.S. Cl.
CPC .......... *A61K 31/506* (2013.01); *A61K 31/404* (2013.01); *A61K 31/4168* (2013.01); *A61K 31/437* (2013.01); *A61K 31/4365* (2013.01); *A61K 31/4439* (2013.01); *A61P 25/28* (2018.01)

(58) Field of Classification Search
CPC ....................................................... A61P 25/28
See application file for complete search history.

(56) References Cited

U.S. PATENT DOCUMENTS

2006/0030559 A1    2/2006    Buettelmann et al.

FOREIGN PATENT DOCUMENTS

| KR | 101439203 B1 | 9/2014 |
|---|---|---|
| WO | 02068417 A2 | 9/2002 |
| WO | 2009076529 A1 | 6/2009 |
| WO | 2014/060384 A1 | 4/2014 |

OTHER PUBLICATIONS

Mihov et al., Negative Allosteric Modulators of Metabotropic Glutamate Receptors Subtype 5 in Addiction: a Therapeutic Window, 2016, International Journal of Neuropsychopharmacology, 19(7), pp. 1-11 (Year: 2016).*
Greer, D., Aspirin and Antiplatelet Agent Resistance Implications for Prevention of Secondary Stroke, 2010, CNS Drugs, 24(12), pp. 1027-1040 (Year: 2010).*
Powers et al., Guidelines for the Early Management of Patients With Acute Ischemic Stroke: 2019 Update to the 2018 Guidelines for the Early Management of Acute Ischemic Stroke A Guideline for Healthcare Professionals From the American Heart, 2019, Stroke, e344-e418 (Year: 2019).*
Szydlowska, et al.; European Journal of Pharmacology; 554 (2007) 18-29.
Movsesyan V.A., et al.; The Journal of Pharmacology and Experimental Therapeutics, 2001; vol. 296, No. 1; pp. 41-47.
Makarewicz D., et al.; Folia Neuropathologica 2015; vol. 53, No. 4; pp. 301-308.
Makarewicz et al. "Neuroprotective potential of group I metabotropic glutamate receptor antagonists in two ischemic models." Neurochem. Int. 48: 485-490, 2006.
Raboisson et al. "Discovery and characterization of AZD9272 and AZD6538—Two novel mGluR5 negative allosteric modulators selected for clinical development." Bioorg. & Med. Chem. Lett. 22: 6974-6979, 2012.
Zhang et al., J. Med. Chem., Feb. 13, 2014, vol. 57, No. 3, pp. 861-877.
Jeaschke et al., J. Med. Chem., Feb. 12, 2015, vol. 58, No. 3, pp. 1358-1371.
PCT International Search Report and Written Opinion dated Jul. 8, 2016 from corresponding Application No. PCT/SE2016/050264, 13 pages.
Jiang, L. et al., Discovery of potential negative allosteric modulators of mGluR5 from natural products using pharmacophore modeling, molecular docking, and molecular dynamics simulation studies, Can. J. Chem., 93: 1199-1206, 2015.
Wagner, G. et al., Hit-to-lead optimization of disubstituted oxadiazoles and tetrazoles as mGluR5 NAMs, Bioorganic & Medicinal Chemistry Letters, 20: 3737-3741, 2010.
Zhou, H. et al., Discovery and structure-activity relationship of 1,3-cyclohexyl amide derivatives as novel mGluR5 negative allosteric modulators, Bioorganic & Medicinal Chemistry Letters, 23: 1398-1406, 2013.
Mueller, R. et al., Discovery of 2-(2-Benzoxazoyl amino)-4-Aryl-5-Cyanopyrimidine as Negative Allosteric Modulators (NAMs) of Metabotropic Glutamate Receptor 5 (mGlu5): From an Artificial Neural Network Virtual Screen to an In Vivo Tool Compound, ChemMedChem, 7: 406-414, 2012.

* cited by examiner

*Primary Examiner* — Kortney L. Klinkel
*Assistant Examiner* — Tori Strong
(74) *Attorney, Agent, or Firm* — Dinsmore & Shohl LLP; Weston R. Gould

(57) ABSTRACT

The present disclosure relates to the use of negative allosteric modulators (NAMs) of the metabotropic glutamate receptor 5 (mGluR5) in the treatment of a mature brain damage, such as damage after stroke.

11 Claims, 10 Drawing Sheets

NEGATIVE ALLOSTERIC MODULATORS OF MGLUR5 FOR USE IN THE TREATMENT OF MATURE BRAIN DAMAGES

FILED OF THE INVENTION

The present invention relates to the use of Negative Allosteric Modulators (NAMs) of metabotropic Glutamate Receptor subtype 5 (mGluR5) in the treatment of mature brain damages.

BACKGROUND

Glutamate, which is a neurotransmitter in the central nervous system of mammals, interacts with different glutamate receptors. Some of these receptors are metabotropic glutamate receptors (mGluR), of which there are eight different subtypes divided into three groups. Group I includes i.a. subtype 5, mGluR5.

An allosteric modulator is a substance which indirectly modulates the effects of another substance (usually a ligand, which may be an agonist or antagonist, and in the present case glutamate) at a target protein, such as a receptor and in this specific case the metabotropic glutamate receptor subtype 5. Allosteric modulators bind to a site on the receptor distinct from that of the orthosteric binding site(s), which is/are receptor ligand binding site(s) for agonists or antagonists. Often, the allosteric modulator induces a conformational change within the protein structure. A negative allosteric modulator (NAM) is an attenuator, and a positive allosteric modulator (PAM) is an enhancer, of the effects of the other substance acting at the orthosteric site(s). A NAM of mGluR5 modulates the binding of glutamate to the glutamate receptor subtype 5. A NAM of mGluR5 is thus not equivalent with an antagonist of the metabotropic glutamate receptor subtype 5.

In experimental studies, it has earlier been shown that at least some NAMs of mGluR5, such as 2-methyl-6-phenyl-ethynylpyridine (MPEP), have a neuroprotective action when administered early after a brain injury. However, according to these earlier studies, the treatment must be initiated very early after the injury has occurred, in the time span of within minutes to up to 4 hours after injury. Also, data are contradictory, some showing brain protection by mGluR5 antagonists and mGluR5 NAMs while others demonstrate the opposite effect or protection by mGluR5 agonists. Hence the neuroprotective therapeutic time window of the mGluR5 NAMs is narrow and presumably reflect inhibition of acute excitotoxicity during the insult.

The disclosures of all documents referred to throughout this application are incorporated herein by reference.

SUMMARY OF THE INVENTION

The present invention relates to a negative allosteric modulator (NAM) of the metabotropic glutamate receptor 5 (mGluR5) for use in the treatment of a mature brain damage.

The present invention further relates to use of a negative allosteric modulator (NAM) of the metabotropic glutamate receptor 5 (mGluR5) in the production of a pharmaceutical composition for treatment of a mature brain damage.

The present invention further relates to a method of treating a mature brain damage in a patient, wherein a therapeutically effective amount of a negative allosteric modulator (NAM) of the metabotropic glutamate receptor 5 (mGluR5) is administered to the patient.

DETAILED DESCRIPTION OF THE INVENTION

As already mentioned, the present invention relates to the use of Negative Allosteric Modulators (NAMs) of metabotropic Glutamate Receptor subtype 5 (mGluR5) in the treatment of a matured brain damage. The skilled person knows that there are several different NAMs of mGluR5. Examples of negative allosteric modulators (NAMs) of metabotropic glutamate receptor subtype 5 (mGluR5) that have been described earlier and that can be used in accordance with the present invention are listed in Table 1 below. In Table 1, the different NAMs have been grouped into two chemotypes; some compounds belonging to the alkyne series, i.e. compounds with an acetylenic backbone structure, and others to the non-alkyne series, i.e. compounds with a non-acetylenic backbone structure. The compounds belonging to the alkyne series all have the generalized structure:

wherein the meaning of $R_1$ and $R_2$, respectively, are from Table 1.

TABLE 1

| | | Names and chemical structures of known mglur5 NAMs | |
|---|---|---|---|
| Trade name(s) | Chemical name | Prior art disclosing the compound | Chemical structure |
| | | Alkyne series | |
| AFQ056 Mavoglurant SIN011 | (3aR,4S,7aR)-Octahydro-4-hydroxy-4-[2-(3-methylphenyl)ethynyl]-1H-indole-1-carboxylic acid methyl ester | Cole P. Drugs of the Future 37:7 | 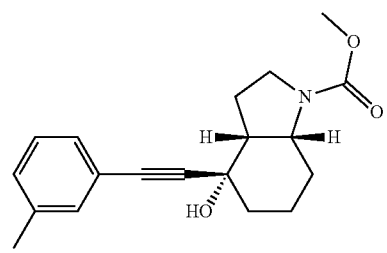 [SMILES: COC(=O)N1CC[C@@H]2[C@H]1CCC[C@@]2(O)C#Cc1cccc(C)c1] |

TABLE 1-continued

Names and chemical structures of known mglur5 NAMs

| Trade name(s) | Chemical name | Prior art disclosing the compound | Chemical structure |
|---|---|---|---|
| RG7090 Ro4917523 Basimglurant SIN014 | 2-chloro-4-((2,5,-dimethyl-1-(4-fluoro-phenyl))-1H-imidazol-4-yl) ethynyl)pyridine | US 2012-035222 | 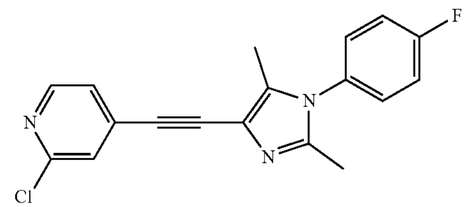 [SMILES: Cc1nc(C#Cc2ccnc(Cl)c2)c(C)n1-c1ccc(F)cc1] |
| CTEP SIN013 | 2-chloro-4-((2,5,-dimethyl-1-(4-fluoro-phenyl))-1H-imidazol-4-yl) ethynyl)pyridine | Lindemann et al. 339:474 (2011) | 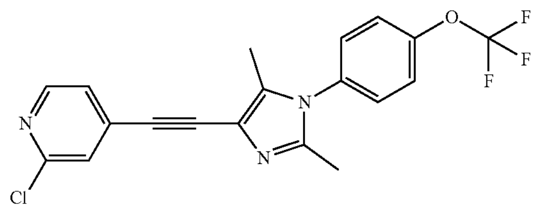 [SMILES: Cc1nc(C#Cc2ccnc(Cl)c2)c(C)n1-c1ccc(OC(F)(F)F)cc1] |
| STX107 SIN017 | 3-fluoro-5-(5-((2-methylthiazol-4-yl) ethynyl)pyridin-2-yl)benzonitrile | Zhou H et al. Bioorg Med Chem Lett 23:1398 (2013) | 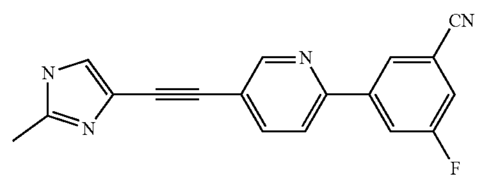 [SMILES: Cc1nc(C#Cc2ccc(-c3cc(F)cc(C#N)c3)nc2)c[nH]1] |
| ADX-48621 Dipraglurant SIN008 | 6-fluoro-2-[4-(pyridin-2-yl)-3 butynylimidazo[1,2-a]pyridine | Sciamanna G et al., Neuropharmacology 85:440 (2014) | 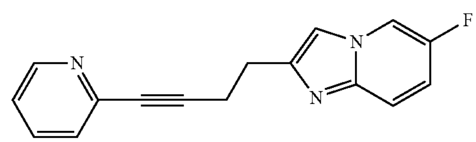 [SMILES: Fc1ccc2nc(CCC#Cc3ccccn3)cn2c1] |
| GRN-529 | ((4-difluoromethoxy-3-(pyridine-2-ylethynyl)phenyl)5H-pyrrolo[3,4-b] pyridine-6(7H)-yl methanone) | US 2010-0273772 | 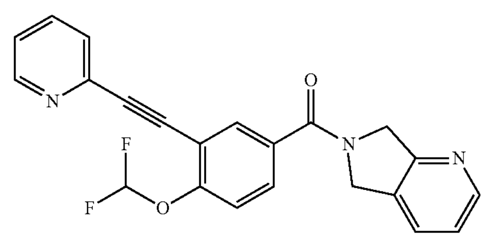 [SMILES: O=C(c1ccc(OC(F)F)c(C#Cc2ccccn2)c1)N1Cc2cccnc2C1] |
| MFZ 10-7 | 3-fluoro-5-[(6-methylpyridin-2-yl) ethynyl]benzonitrile | Keck TM et al, ACS Med Chem Lett 3:544 (2012) | 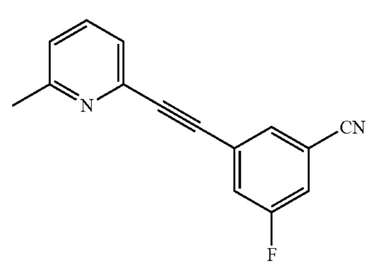 [SMILES: Cc1cccc(C#Cc2cc(F)cc(C#N)c2)n1] |
| MRZ-8676 | 6,6-dimethyl-2-phenylethynyl-7,8-dihydro-6H-quinolin-5-one ethynyl]benzonitrile | Dekundy et al., Neurotransmission Neurotransmission 118:1716 (2011) Biol. 19:195 (2012) | 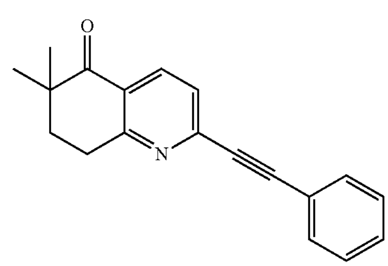 [SMILES: CC1(C)CCc2nc(C#Cc3ccccc3)ccc2C1=O] |

TABLE 1-continued

Names and chemical structures of known mglur5 NAMs

| Trade name(s) | Chemical name | Prior art disclosing the compound | Chemical structure |
|---|---|---|---|
| Non-alkyne ligands | | | |
| Fenobam SIN010 | N-(3-chlorophenyl)-N0-(4,5-dihydro-1-methyl-4-oxo-1H-imidazole-2-yl)urea | Porter RH, J Pharmacol Exp Ther 315:711 (2005) | 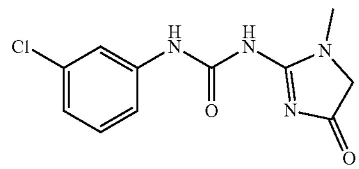 [SMILES: CN1CC(=O)N=C1NC(=O)Nc1cccc(Cl)c1] |
| | 1-(5-Chloro-3-thienyl)-3-(1-methyl-4-oxo-2-imidazolin-2-yl)urea) | Jaeschke G et al Bioorg, Med Chem Lett 17:1307 (2007) | |
| | 2-oxo-2,3-dihydrobenzooxazole-4-carboxylic acid (6-methyl-pyridin-2-yl)-amide | Cecarelli et al. Bioorg Med Chem Lett 17, 1302 (2007) | |
| AZD-6538 SIN015 | 3-fluoro-5-(3-(5-fluoropyridin-2-yl)-1,2,4-oxadiazol-5-yl)benzonitrile | Raboisson P et al., Bioorg, Med Chem Lett 22:6974 (2012) | 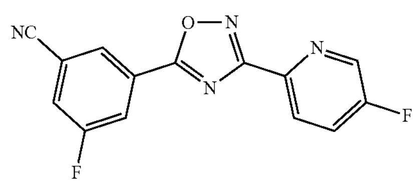 [SMILES: N#Cc1cc(F)cc(-c2nc(-c3ccc(F)cn3)no2)c1] |
| AZD-9272 | 6-[5-(3-cyano-5-fluorophenyl)-1,2,4-oxadiazol-3-yl]pyridine-3-carbonitrile | Raboisson P et al., Bioorg, Med Chem Lett 22:6974 (2012) | 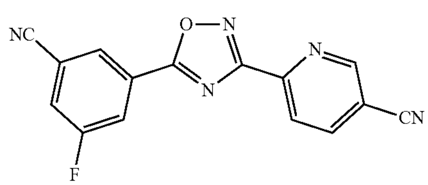 [SMILES: N#Cc1ccc(-c2noc(-c3cc(F)cc(C#N)c3)n2)nc1] |
| | 3-Fluoro-5-(2-(pyridin-2-yl)-7,8-dihydro-4H-oxazolo[4,5-c] azepin-5(6H)-yl)benzonitrile | Burdi et al., J Med Chem. 53, 7107 (2010) | |

TABLE 1-continued

Names and chemical structures of known mglur5 NAMs

| Trade name(s) | Chemical name | Prior art disclosing the compound | Chemical structure |
|---|---|---|---|
| VU0431316 | 4-chloro-N-(6-(pyrimidin-5-yloxy) pyrazin-2-yl)picolinamide | Bates BS et al., Bioorg Med Chem 24:3307 (2014) | 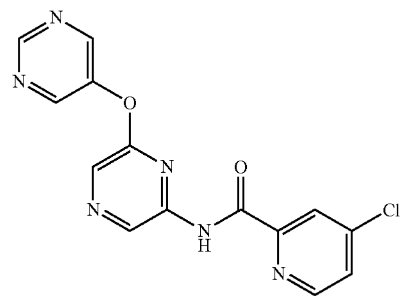 [SMILES: O=C(Nc1cncc(Oc2cncnc2)n1)c1cc(Cl)ccn1] |
| VU0366058 | 2-[(1,3-benzoxazol-2-yl)amino]-4-(4-fluorophenyl)pyrimidine-5-carbonitrile | Mueller R et al. Chem Med Chem 7:406 (2012) | 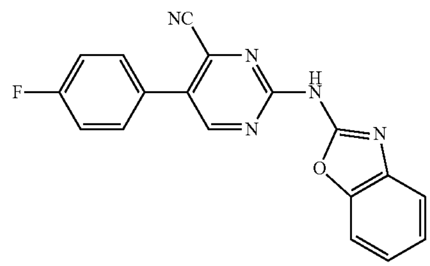 [SMILES: N#Cc1nc(Nc2nc3ccccc3o2)ncc1-c1ccc(F)cc1] |
| | (1R,2R)-N-(4-(6-isopropylpyridin-2-yl)-3-(2-methyl-2H-indazol-5-yl)isothiazol-5-yl)-2-methylcyclopropane-carboxamide | Hou J et al., Bioorg Med Chem Lett 23:1249 (2013) | |
| | | WO 2007/072095 Nogradi K et al., Bioorg Med Chem Lett 24:3845 (2014) | |
| | | Weiss JM et al, Bioorg, Med Chem Lett 21:4891 (2011) | |

TABLE 1-continued

Names and chemical structures of known mglur5 NAMs

| Trade name(s) | Chemical name | Prior art disclosing the compound | Chemical structure |
|---|---|---|---|
| | 6-bromo-pyrazolo[1,5-a]pyrimidin-2-yl)-(1-methyl-3,4-dihydro-1H-isoquinolin-2-yl)-methanone | WO 2011/064237 | |
| | | Panka C et al., Bioorg Med Chem Lett 20:184 (2010) | |
| GSK2210875 | [(1R)-1-(6-methyl-[1,3]thiazolo[2,3-e][1,2,4]triazol-5-yl)ethyl] N-phenylcarbamate | Pilla M et al., Bioorg Med Chem Lett 20:7521 (2010) | 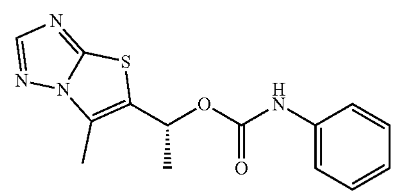 [SMILES: Cc1c([C@@H](C)OC(=O)Nc2ccccc2)sc2ncnn12] |
| | 5-methyl-pyrazine-2-carboxylic acid [3-(3-fluoro-benzoylamino) adamantan-1-yl]-amide as well as 6 derivatives thereof | WO 2010/011570 A1 | |

The skilled person is also familiar with test methods that may be used to decide whether or not a specific compound is a NAM of mGluR5. Examples of such test methods (Vranesic et al, (2014) Bioorg. Med. Chem, 22:5790-5803) are radioligand displacement (Gasparini et al, (2002) Bioorg Med Chem Lett, 12:407-409), inhibition of cellular $Ca^{2+}$ mobilization (Widler et al, (2010) J. Med. Chem, 53:2250-2263), and inhibition of inositolphosphate hydrolysis (Litschig et al., (1999) Mol. Pharm, 55:453-461), assays In some embodiments of the present invention, the NAM used is selected from the group consisting of the following compounds:

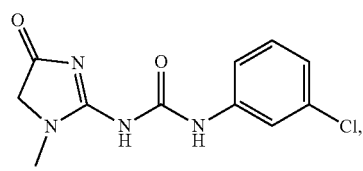

-continued

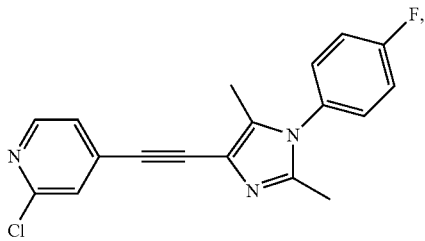

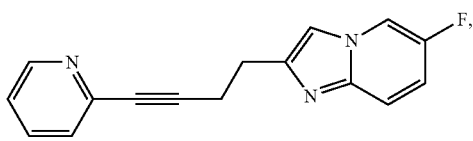

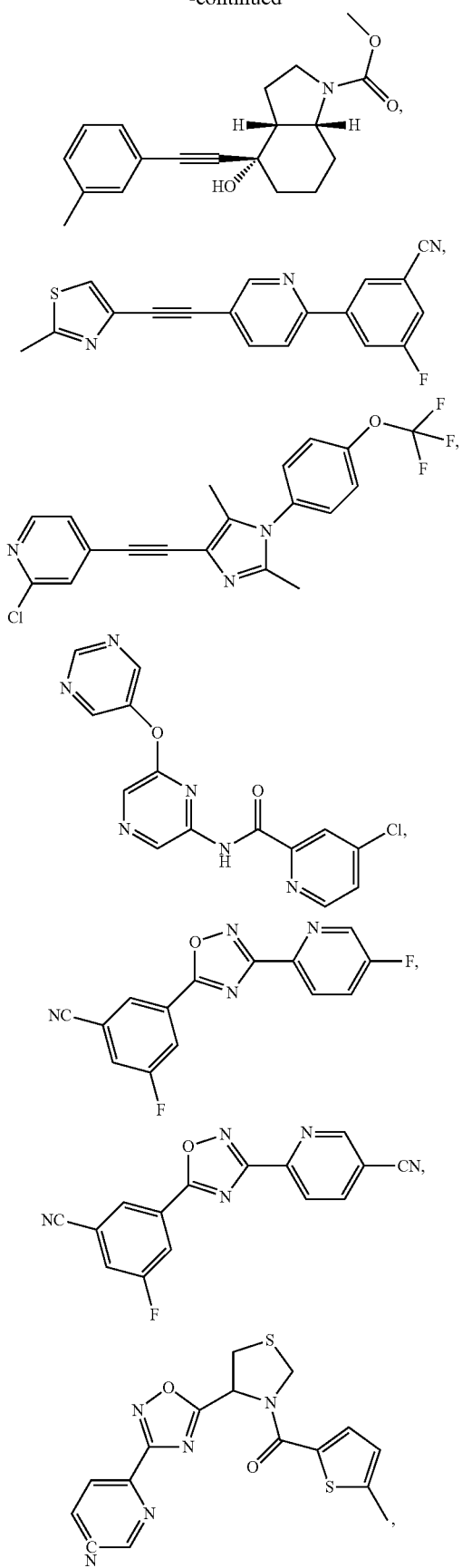
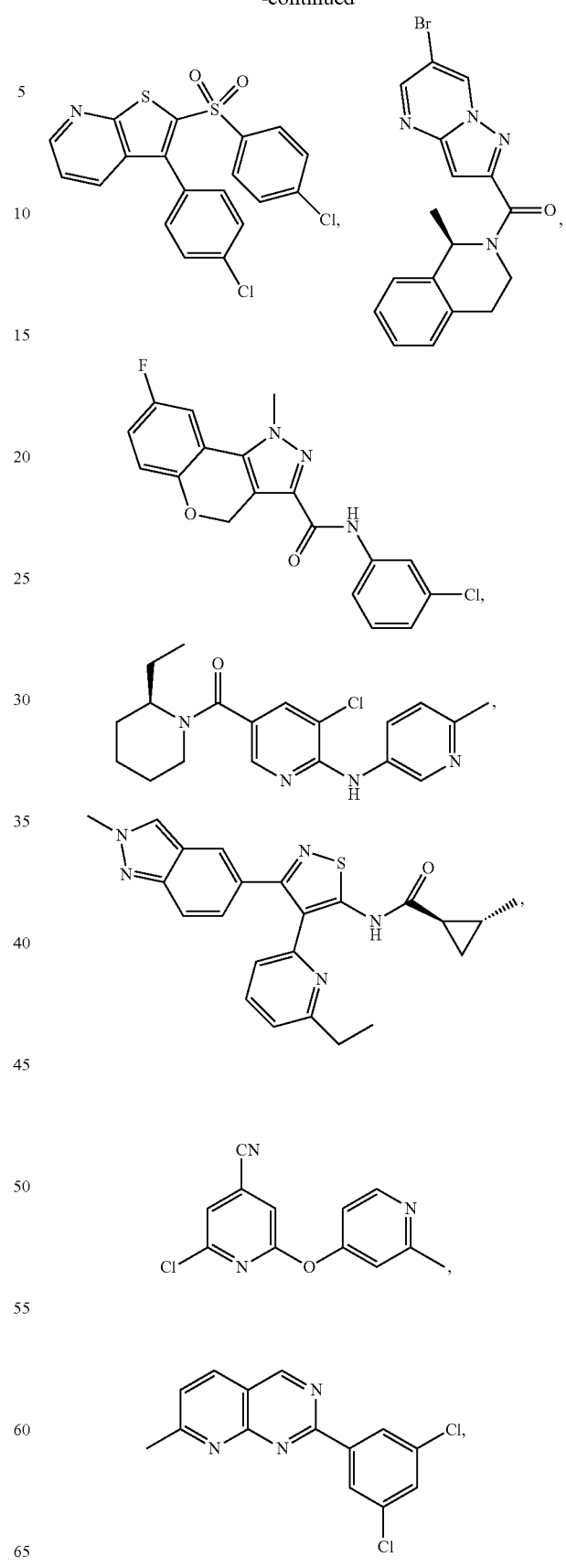

-continued

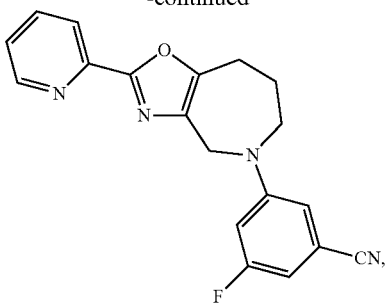

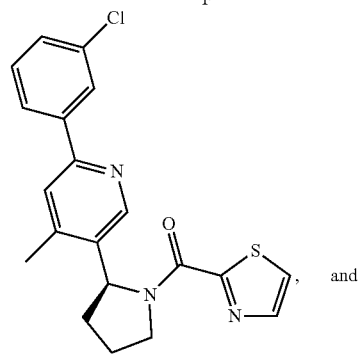

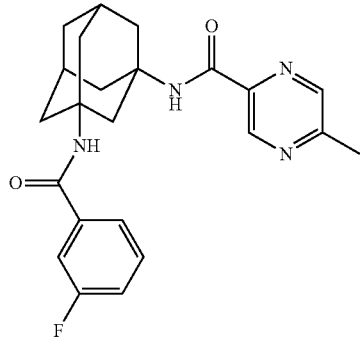

In some embodiments, the NAM used is:

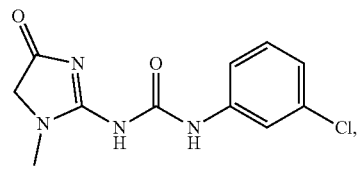 [SMILES: CN1CC(=O)N=C1NC(=O)Nc1cccc(Cl)c1]

which is denoted SIN010 in the Examples below.
In some embodiments, the NAM used is:

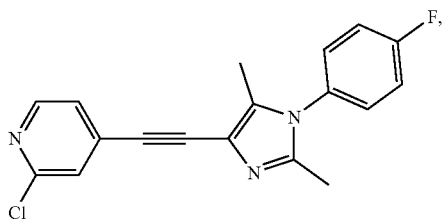 [SMILES: Cc1nc(C#Cc2ccnc(Cl)c2)c(C)n1-c1ccc(F)cc1]

which is denoted SIN014 in the Examples below, and which is a close analogue to the compound denoted SIN013 in the Examples below.

In some embodiments, the NAM used is:

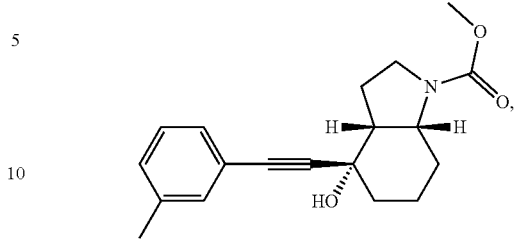

which is denoted SIN011 in the Examples below.
In some embodiments, the NAM used is:

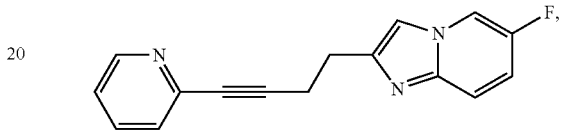

which is denoted SIN008 in the Examples below.
In some embodiments, the NAM used is:

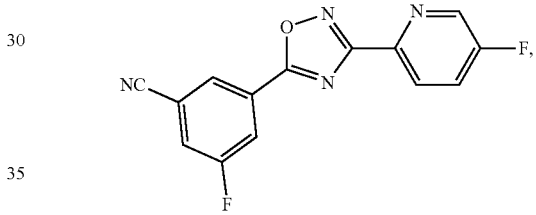

which is denoted SIN015 in the Examples below.

In some embodiments, the NAM used is selected from the group consisting of pharmaceutically acceptable salts and solvates of any of the specific 20 compounds mentioned above.

In this context, pharmaceutically acceptable salt means a salt of a NAM according to the invention, which does not cause significant irritation to a patient to which it is administered and does not abrogate the biological activity and properties of the compound.

Solvates of the compounds described herein may be used for the purpose of altering the chemical and physical properties, such as melting point, chemical reactivity, apparent solubility, dissolution rate, optical and electrical properties, vapor pressure, and density. If the incorporated solvent is water, the solvates are also commonly known as hydrates.

In some embodiments, it is possible to use a compound that which upon administrated to a human is metabolized to any of the NAMs mentioned above. The NAM according to the invention is then used indirectly.

Since these compounds are previously known, the skilled person knows how to synthesize them.

According to the present invention, the NAM of mGluR5 is used in the treatment of a mature brain damage.

In the context of the present invention, the term "mature brain damage" refers to any brain damage or brain injury that is established and thus that does not progress further. This occurs once cell death in the brain has subsided. Brain damage, or brain injury, is related to the destruction or degeneration of brain cells, and may be caused by a number of different conditions, illnesses and/or injuries, and in the context of the present invention the term brain damage includes both iatrogenic and non-iatrogenic brain damages.

In some embodiments, the mature brain damage may have been caused by a stroke. The stroke may be selected from the group consisting of ischemic stroke, hemorrhagic stroke and transient ischemic attack. In the case of a hemorrhagic stroke, which may be caused by hypertension or the rupture of a weakened blood vessel, including aneurysms and arteriovenous malformations.

The mature brain damage caused by a stroke may have progressed into one or more condition(s) or disorder(s) selected from the group consisting of cognitive impairment, sensorimotor dysfunction, depression or fatigue. The cognitive impairment may encompass deficits of attention, memory and working memory, judgement and evaluation, reasoning and "computation", problem solving and decision making, and comprehension and production of language, and may involve one or more condition(s) selected from the group consisting of aphasia, memory dysfunction and hemispatial neglect.

In some embodiments, the mature brain damage has been caused by cardiopulmonary arrest, an acute brain injury, a traumatic brain injury (TBI), surgery, radiation, vascular dementia, epileptic seizure, cerebral vasospasms, and/or hypoxia of the brain as a result of cardiopulmonary arrest or near drowning.

When the mGluR5 NAM according to the invention is administered to a patient suffering from a mature brain damage, it will lead to an improved recovery of the patient's brain function, compared to how the situation would be without administration of the NAM. The treatment according to the present invention is to be initiated once a mature brain damage has occurred. Once the brain damage or brain injury does not progress further, cell death in the brain has subsided and a neuroprotective treatment is no longer effective. The treatment according to the present invention shall thus be initiated once a neuroprotective treatment no longer has any significant effect on the damage. In some embodiments the treatment shall therefore not be initiated until at least 4 hours have passed since the acute brain damage occurred. In some embodiments the treatment is initiated no earlier than 5 hours after the acute brain damage occurred. In some embodiments the treatment is initiated no earlier than 6 hours after the acute brain damage occurred. In some embodiments the treatment is initiated no earlier than 8 hours after the acute brain damage occurred. When the acute brain damage, such as an acute stroke, is treated with a thrombolytic agent, i.e. with fibrinolytic therapy, or by mechanical removal of the occlusion preventing blood flow in the brain arteries, the timing of the start of the treatment according to the invention may coincide with the termination of the fibrinolytic therapy or after mechanical removal of the occlusion. When recanalization—either pharmacological or surgical—is used, the treatment in accordance with the invention can be initiated when the recanalization is performed or shortly after. The sooner the treatment is initiated, the better. However, it is also possible to initiate the treatment much longer after the acute brain damage has been established, i.e. long after the initial brain damage or injury resulting in the mature brain damage. It is possible to initiate the treatment, days, weeks, months or even years after the establishment of the mature brain damage. This later initiation of the treatment in accordance to the invention is similar to when regular physical therapy might be considered even during later stages of a mature brain damage.

The treatment in accordance with the invention can be life long. Alternatively, the treatment may be continued during 2-7 days, during 2-4 weeks, during 2-4 months or during one or a few years.

The treatment according to the invention may be combined with one or more other therapies. For example, it may be combined with transcranial magnetic stimulation (Pollock et al, (2014) Interventions for improving upper limb limb function after stroke (review), Chocrane Database Sys Rev, 12:11). Alternatively, the treatment according to the invention may be combined with electrical brain stimulation (Pollock et al, 2014), such electrical stimulation may be either anodal or cathodal. The treatment according to the invention may also be combined with physical therapy, rehabilitative training including computer-assisted virtual reality or robotics-assisted training and therapies (Laffont et al. Annals of Physical and Rehabilitation Medicine (2014) 57:543-551). Such physical therapy may be constraint induced therapy. This is further discussed in Example 2.

The term "treatment" used herein relates to treatment in order to cure or alleviate a disease or a condition.

The term "patient", as it is used herein, relates to any human or non-human mammal in need of treatment according to the invention.

The term "therapeutically effective amount" relates to an amount that will lead to the desired therapeutical effect, i.e. to a beneficial effect on the mature brain damage that is to be treated.

The NAM according to the invention or used according to the invention may be included in a pharmaceutical composition or formulation. Such a composition may include pharmaceutical excipients and/or adjuvants, including diluants and carriers. The pharmaceutical composition faciliates administration of the NAM according to the invention to a patient. The pharmaceutical composition may be manufactured in a manner that is itself known, e.g., by means of conventional mixing, dissolving, granulating, dragee-making, levigating, emulsifying, encapsulating, entrapping or tableting processes.

Administration of the NAM or the pharmaceutical composition according to the invention may be performed in any conventional way, Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can be administered in sustained or controlled release dosage forms, for prolonged administration.

BRIEF DESCRIPTION OF THE DRAWINGS

In the examples below, reference are given to the appended figures, on which:

FIG. 1A: Functional recovery after 12 days of treatment that started 2 days after stroke. FIG. 1B: Infarct size after stroke. FIG. 1C: Time course of functional recovery. SIN007 (S); vehicle (V). FIG. 1D: The persistence of recovery after 5 days of SIN007 treatment is discontinued.

FIG. 2A: Functional recovery after 5 days of treatment. FIG. 2b: Infarct size after stroke. FIG. 2C: Five days treatment starting at 2 days (2 d) or 10 days (10 d) after stroke. FIG. 2D: Pretreatment with the mGluR5 positive allosteric modulator SIN 006; (N-Cyclobutyl-6-[2-(3-fluorophenyl)ethynyl]-3-pyridinecarboxamide hydrochloride); VU0360172, one hour prior to treatment with SIN 007 for 6 days. FIGS. 2E and 2F: Housing mice in an enriched environment for 5 days after stroke, enhances recovery of brain function, an effect obliterated with a concomitant treatment with SIN006 (FIG. 2E) but further enhanced by concomitant treatment with SIN007 (FIG. 2F), respectively.

FIG. 3A: Effect of SIN 008 [6-Fluoro-2-[4-(pyridin-2-yl)-3-butynyl]imidazo[1,2-a]pyridine, ADX 70084] on functional recovery in the rat. FIG. 3B: Effects of SIN011 ([3aS,5S,7aR]-methyl 5-hydroxy-5-(m-tolylethynyl) octahydro-1H-indole-1-carboxylate, mavoglurant) and, FIG. 3C: the effect of two doses of SIN013 ([2-chloro-4-((2,5-dimethyl-1-(4-(trifluoromethoxy)phenyl))-1H-imidazol-4-yl)ethynyl)pyridine, CTEP) on functional recovery in the mouse. FIG. 3D: The effect of SIN013 on functional recovery of wild type and mGlur5 KO rats.

EXAMPLES

Figure 1A:
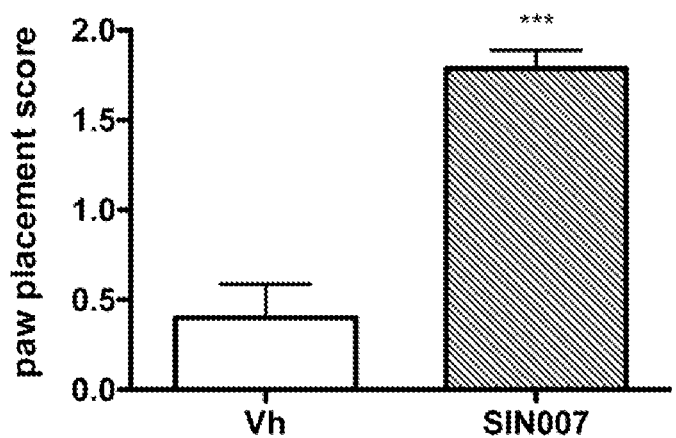
FIGS. 1A-D illustrate the effect of the prototypic mGluR5 negative allosteric modulator with an acetylenic backbone structure: SIN007; 3((2-methyl-1,3-thiazol-4-yl)ethylnyl) pyridine; MTEP on functional recovery after stroke in the rat, compared to vehicle (Vh) treatment.

The examples below are given in order to illustrate the invention and in particular specific embodiments thereof.

Example 1: Effects of a Prototypic Alkyne mGluR5 NAM, SIN007, on Functional Recovery after Stroke in the Rat Experimental Procedures Animals. All experiments were carried out with the approval of the Malmö-Lund animal review board and according to the ARRIVE guidelines. Animals were housed under reverse light conditions, with the testing performed during the dark period when the rats are active. The experiments were carried out on male Sprague Dawley rats (11 weeks of age, Charles River, Scanbur A/S Karlslunde, Denmark). The studies were subjected to randomization and carried out in a blinded fashion to the investigators who performed the surgeries and behavioral assessment.

Materials. (3-[(2methyl-1,3-thiazol-4-yl)ethynyl]pyridine, MTEP) was synthesized by Beijing Honghui Meditech Co., Ltd, (Beijing, China) and the structure confirmed by $H^1$-NMR. It was dissolved in 0.3% Tween 80 in saline.

Administration of compound. The compound was injected as a bolus dose of 1 ml/kg into the lower quadrant of the abdomen.

Experimental stroke. The animals were anesthetized by isoflurane (approximately 2% in 02 under spontaneous ventilation) and placed into stereotaxic frame. Temperature was monitored during surgery using a rectal temperature probe and animals were kept at 37.0-37.5±0.2° C. by means of a heating pad with feedback control. A sagittal skin incision was made and subcutaneous connective tissue was removed and the skull was dried. Thereafter, the photosensitizer dye Rose Bengal (0.5 mL at 10 mg/mL) was infused in the tail vein. Two minutes after injection, the skull was illuminated with cold light (Schott, KL 1500 LCD) on an area of 8 to 4.5 mm for 15 min (from +4 to −4 mm antero-posterior and from 0.5 to 5 mm on the left from bregma). Thereafter the tail and the scalp incisions were sutured and the rats transferred to their home cage. The functional deficit was assessed 2 h after the onset of the stroke using the limb placement test and only the animals having a score 0, for both fore- and hindlimb contralateral to the brain damaged hemisphere were used for the study.

Test of neurological function. The paw placement test. The cortical damage inflicted by the phothrombosis, causes a deficit due to neuronal loss in the sensori-motor area and depression of functions in neuronal networks in the vicinity of the lesion. This is displayed by loss of response in the paw placement test. This test provides information on the tactile/proprioceptive response to limb stimulation. Animals were placed with all 4 paws on the table top, and the paws to be tested along the edge. The rat was moved over the edge so the paws to be tested loose contact with the table surface. The ability of the animals to place the limb back onto the table surface when the rat was moved towards the edge was evaluated. Importantly, the head was held at 45° angle, so that visual and whisker/snout stimulation was prevented. A prompt placement of the limb onto the table was scored as 1. Incomplete placing of the limb was scored as 0.5, and complete extension of the limb and paw was scored as 0. In order to obtain groups with a similar functional deficit prior to treatment of the animals with drugs or vehicle, selective sorting was performed on day 2 after experimental stroke, a time point of recovery when the infarct development had subsided. Hence, only animals that showed a severe deficit in the paw placement (score=0) entered the studies.

Tissue collection. The animals were deeply anesthetized (isoflurane) and perfusion-fixed with 4% paraformaldehyde (PFA) solution. Brains were collected and immersed in 4% PFA solution for 4 h, then transferred into a 25% sucrose phosphate buffer solution (0.1 M $NaH_2PO_4$, 0.1 M $Na_2HPO_4$) and stored at 4° C. Brains were then cut in 30 µm slices using a microtome and one slice was kept each 1 mm for infarct size measurement. The others were kept for immunohistochemistry and immunofluorescence. All the slices were stored in anti-freeze solution (30% ethylene glycol, 30% glycerol, 0.01 M $NaH_2PO_4$, 0.03 M $Na_2HPO_4$) at −20° C.

Immunohistochemistry. Free-floating brain slices were rinsed three times in PBS (phosphate buffer saline) and quenched in 3% $H_2O_2$ and 10% MetOH for 15 minutes. After washing in PBS, the sections were blocked with blocking solution (5% normal donkey serum, Jackson ImmunoResearch, UK and 0.25% Triton X-100 in PBS) for one hour at room temperature. The sections were incubated overnight at 4° C. with a monoclonal mouse anti-NeuN antibody (A60/MAB377, Millipore) at the dilution of 1:1500. Following three rinses with 1% normal donkey serum and 0.25% Triton X-100 in PBS, the sections were then incubated with appropriate secondary biotinylated antibodies (donkey anti-rabbit/mouse, Vector Laboratories, USA) at a dilution of 1:400 in blocking solution for 90 minutes at room temperature (RT). Visualization was achieved via the Vectorstain ABC kit (Vector) using 3,3-diaminobenzidine-tetrahydrochlorid (DabSafe, Saveen Werner, Sweden), 8% NiCl and 3% $H_2O_2$.

Infarct measurements. Bright field pictures were acquired using an Olympus BX60 microscope (Solna, Sweden). Twelve slices 1 mm apart, were scanned, and the non-lesioned area of the infarcted hemisphere and the non-lesioned contralateral hemisphere were outlined and measured using the ImageJ software (National Institute of Health, USA). Infarct volume ($mm^3$) was determined by subtracting the area of the non-lesioned ipsilateral hemisphere from that of the intact contralateral hemisphere, and calculated by volumetric integration for each animal.

Results

Figure 1B:
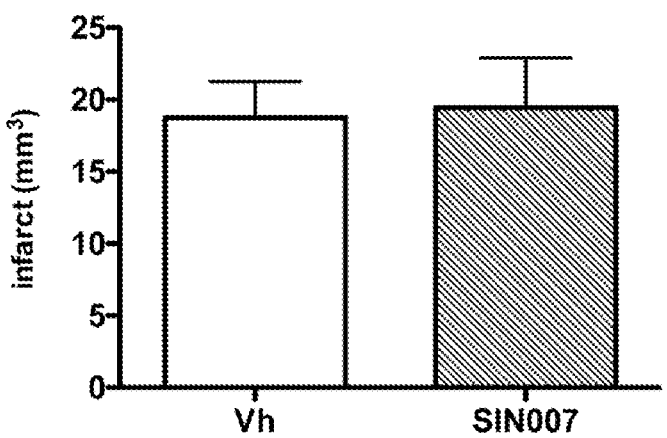
Figure 1C:
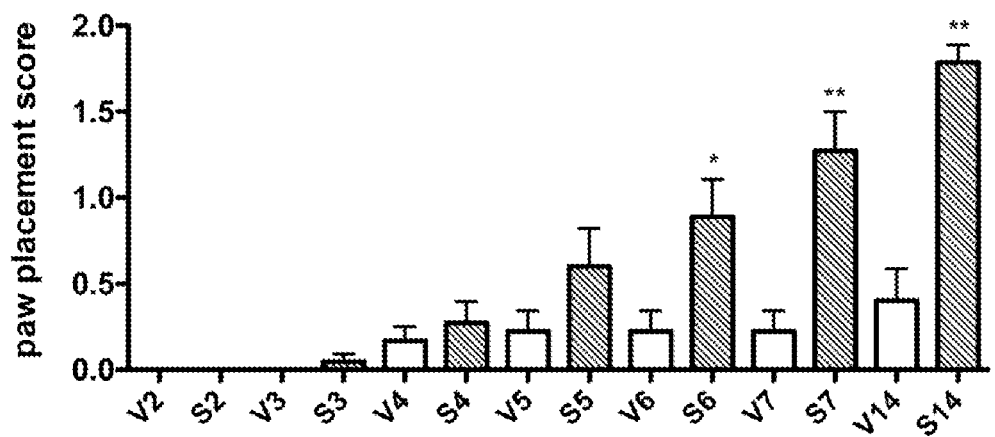
Figure 1D:
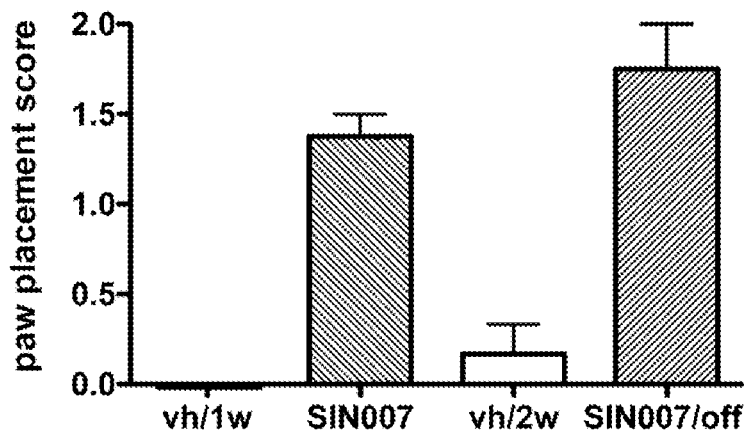

The effect of daily treatment for 5 days with SIN007 (5 mg/kg i.p.) or vehicle (0.3% Tween 80 in saline) starting 2 days after stroke on paw placement score assessed at 14 days after stroke is shown in FIG. 1A. There was an almost complete recovery of paw placement function in the SIN007 treated group (n=7) compared to vehicle (n=5) (p<0.001, Mann Whitney test). FIG. 1B displays the mean infarct size of the animals included in FIG. 1A. The infarct size was 18.8±2.5 $mm^3$ in the vehicle treated animals and 19.5±4.6 $mm^3$ in the SIN007 animals. There was no difference in infarct size between the vehicle and treated groups. FIG. 10 shows the time course of the recovery of function. At least 4 days of treatment with SIN007 is required for a treatment effect and 14 days for a maximal treatment effect (SIN007, s2-s7, n=11; Vh, v2-7, n=11; SIN007, s14, n=7; Vh, v14, n=5). FIG. 1D shows the effect of 5 days of treatment with SIN007 (n=4) and followed by a period of recovery without treatment with SIN007 (SIN007/off). The recovery of function provided by 5 days treatment with SIN007 persist for at least 7 days after termination of the treatment. Taken together the data demonstrated that daily treatment with the mGlur5 NAM starting 2 days after stroke for at least 4 days and preferably 14 days provides a persistent recovery of brain function without providing brain protection. Hence SIN007 provides recovery of function of brain neuronal networks that are depressed but not injured by the stroke.

Example 2. Effect of a Prototypic Alkyne mGluR5 NAM, SIN007, on Functional Recovery after Stroke in the Mouse Experimental Procedure Animals. All experiments were carried out with the approval of the Malmo-Lund animal review board and according to the ARRIVE guidelines. The experiments were carried out on male C57/BL6 mice (8 weeks of age, Charles River Scanbur A/S Karlslunde, Denmark). Studies were subjected to randomization and carried out in a blinded fashion to the investigators who performed the surgeries and behavioral assessment.

Materials were as in Example 1 and the administration of the drug was made as in Example 1. Also the positive allosteric modulator (PAM) for the mGlur5 receptor was SIN006 (N-Cyclobutyl-6-[2-(3-fluorophenyl)ethynyl]-3-pyridinecarboxamide hydrochloride; VU0360172).

Induction of stroke in the mouse. Mice were subjected to unilateral photothrombotic (PT) cortical infarct in the left sensori-motor cortex. During surgery, the body temperature of the animals was kept at 37° C. using a self-regulating heating pad. Animals were anesthetized using 1.5-2.5% isoflurane (Sigma) in 100% 02. The skin above the skull was incised; a fiber optic bundle with a 2.5 mm aperture diameter was connected to a cold light source (CL 1500 ECO, Zeiss, Germany) and adjusted to the stereotaxic coordinates of the sensori-motor cortex, 0.5 mm anterior to bregma and 1.5 mm lateral to midline. One intraperitoneal (i.p.) injection of 0.25 ml Rose Bengal (10 mg/ml in 0.9% saline; Sigma-Aldrich, Germany) was given 5 min before the light was turned on for 20 minutes. Care was taken not to exceed 38° C. at the skull surface, underneath the fiber optic bundle. Post surgery, animals were allowed to awake from anesthesia while on a heating pad and returned to the cages with free access to food pellets and water.

Enriched housing. It is well known that housing of rodents in an enriched environment stimulates the various sensori-motor systems of the brain enhancing recovery after experimental stroke. Enriched housing was accomplished by the following procedure. After selective sorting at day 2 after stroke, mice were randomly distributed into standard (STD, 17 cm×16 cm×34.5 cm) or enriched cages (EE, 30 cm×27 cm×43 cm). Multilevel-enriched cages were equipped with various colored objects such as plastic tunnels, small houses, slides and rodent running wheels; the disposition of the objects was changed every second day. Mice were housed in either standard (2 animals/cage) or enriched cages (6-8 animals/cage) for 12 days. Animals in standard cages were handled similarly except for the housing condition.

Paw placement test. The mouse was held along its rostrocaudal extension on the edge of a bench and both the unilateral front and hind paws were gently pushed along it. The placement of each paw was recorded when the mouse was moved towards the edge. Sensori-motor dysfunction was assessed by using a score of 1, 0.5, and 0: (1)—the paw is immediately placed on the table surface; (0.5)—the limb is extended, but with some movements and attempts to place the paw on the surface of the table; (0)—the paw is totally immobilized, hanging down, with no movement. In order to obtain groups with a similar functional deficit prior to treatment of the animals with drugs or vehicle, selective sorting was performed on day 2 after experimental stroke, a time point of recovery when the infarct development had subsided. Hence, only animals that showed a severe deficit in the paw placement (score=0) entered the studies.

The animals were perfused and immunostained as in Example 1, and the infarct size was assessed as in Example 1.

Results

Figure 2A:
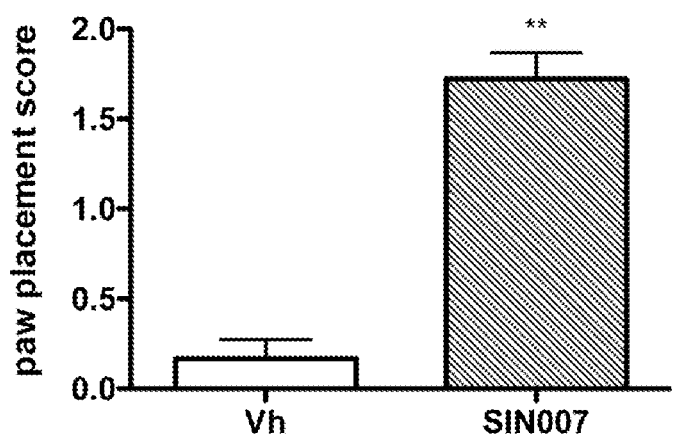
FIGS. 2A-F illustrate the effect of treatment with the prototypic mGluR5 negative allosteric modulator SIN007 on functional recovery after stroke in the mouse, compared to vehicle (Vh) treatment.
Figure 2B:
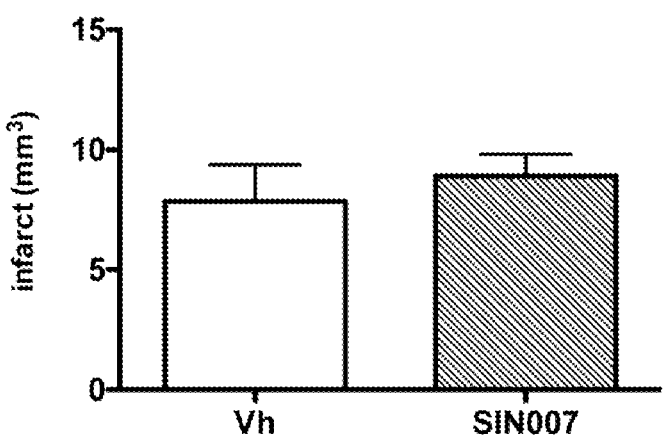
Figure 2C:
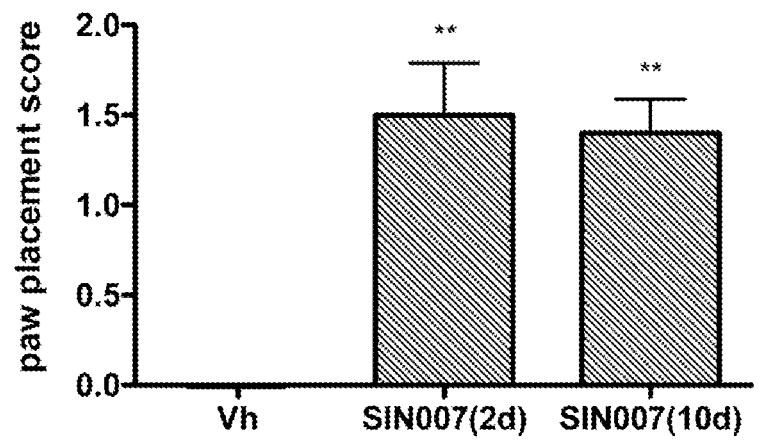
Figure 2D:
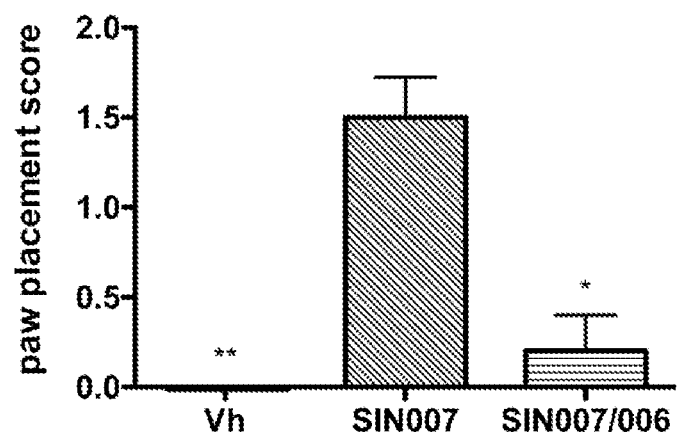
Figure 2E:
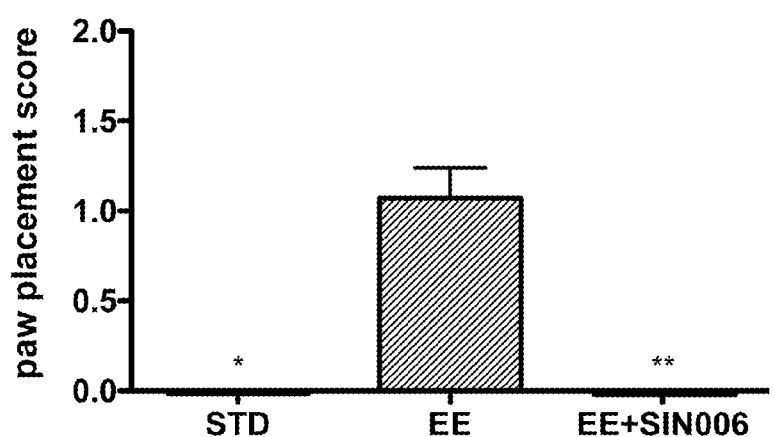

The effect of daily treatment of mice with SIN 007 (5 mg/kg i.p.) for 5 days starting 2 days after stroke is shown in FIG. 2A. A strong recovery enhancing effect is seen in the SIN007 treated animals (n=6) compared to the vehicle treated animals (n=9) (p<0.01, Mann-Whitney). The recovery is not associated with brain protection since the mean infarct size was the same in the two groups. Infarct was 7.9±1.5 $mm^3$ in the vehicle group and 8.9±0.9 $mm^3$ in the SIN007 treated group, FIG. 2B. If treatment is delayed and initiated 10 days after stroke (n=5) the recovery of function is the same as when treatment is initiated at 2 days after stroke (n=4), FIG. 2C, (Vh, n=8) (**indicate p<0.01, Kruskal Wallis Test). To demonstrate that the recovery enhancing effect of SIN007 is mediated by the inhibition of the mGluR5 receptor, mice were treated daily with a positive allosteric modulator of the mGluR5, SIN006 (30 mg/kg p.o.), starting two days after stroke and 1 hour prior to treatment with SIN 007 (5 mg/kg i.p.) (*indicate p<0.05, **p<0.01, Kruskal-Wallis, test), FIG. 2D. Paw placement score was assessed after 5 days of treatment. Animals treated with SIN007 (n=5) recovered paw function compared to vehicle treated animals (n=6) as also shown in FIG. 2A. However, animals treated with SIN006 (n=5) prior to SIN007 did not recover function. The importance of the mGluR 5 receptor inhibition for recovery of brain function after stroke is also shown in an experimental paradigm where brain function is enhanced by physical means, placing the animals in an enriched environment. The enhanced recovery of function evident in animals housed for 5 days in an enriched environment after stroke (n=7) compared to those in standard housing (n=3), FIG. 2E, is completely blocked by concomitant treatment with the mGluR5 agonist, SIN006 (30 mg/kg p.o., (n=4)). This again demonstrates the involvement of mGlur5 receptors in recovery of brain function after stroke (n=4) (indicate p<0.05, Kruskal-Wallis test). Furthermore, treatment with SIN007 (1 mg/kg, i.p. daily for 3 days, n=5) moderately enhances recovery of function, to much the same degree as seen in mice housed in an enriched environment (EE) (n=7). Combining the treatment of SIN007 (1 mg/kg, i.p for 3 days, n=5) with housing in enriched environment, significantly improves recovery, indicating an additive effect of mGlur5 NAM with sensori motor training.

Figure 3A:
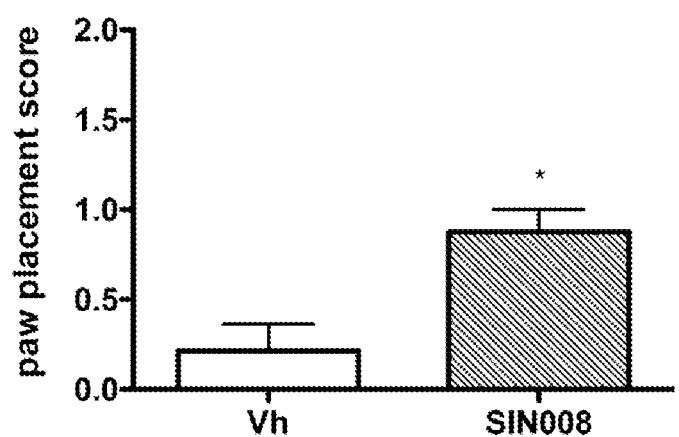
FIG. 3A-D illustrate the effect of the orally available acetylenic mGlur5 NAMs of compounds on functional recovery after stroke.

Example 3. Effect of the Orally Available Alkyne mGluR5 NAMs, SIN008, SIN011, SIN013, SIN014 and SIN017, on Functional Recovery after Stroke Experimental Procedures
Animals. Rats were as in Example 1 and mice as in Example 2. mGluR5 KO rats with inactivated mGluR5 gene were from SAGE, Research Labs, Boyertwon, Pa., USA.
Materials. SIN008 (6-Fluoro-2-[4-(pyridin-2-yl)-3-butynyl]imidazo[1,2-a]pyridine, (ADX49621, dipraglurant), SIN013 [2-chloro-4-[2-[2,5-dimethyl-1-[4-(trifluoromethoxy)phenyl]imidazol-4-yl]ethynyl]pyridine, (CTEP)), SIN014 [2,5-dimethyl-1-[4-fluoro-phenyl]imidazol-4-yl]ethynyl]pyridine, (RG7090, Basmiglurant)), SIN017 (3-fluoro-5-(5-((2-methylthiazol-4-yl)ethynyl)pyridin-2-yl)benzonitrile (STX107)) were all synthesized by Beijing Honghui Meditech Co., Ltd, (Beijing, China). SIN011 (3aR,4S,7aR)-Octahydro-4-hydroxy-4 [2-(3-methylphenyl)ethynyl]-1H-indole-1-carboxylic acid methyl ester, (AFQ056, Mavoglurant)) was from Sv chembiotech, Edmonton, Canada. All compound structures were confirmed by $H^1$—NMR and purity was >97%. SIN011 was suspended in 0.5% hydroxipropylmethylcellulose (HPMC) in distilled water and SIN008 in 20% 2-hydroxipropylcyclodextrin in distilled water, and SIN017, SIN013 and SIN014 in 0.3% Tween80 in saline. The compounds suspended in vehicle were sonicated for 15 minutes in order to obtain a stable suspension.
Administration of the compounds. The compounds were administrated orally (p.o.) by catheters placed in the stomach. The amount of solutions were 0.2 ml/rat and 0.1 ml/mice.
Induction of stroke was as made as in Example 1 for rats and as in Example 2 in mice. Assessment of neurological function was performed as in Example 1 for rats and as in Example 2 for mice. The animals were perfused and immunostained as in Example 1, and the infarct size was assessed as in Example 1.
Results
Treatment with SIN008 (ADX48621, dipraglurant, 30 mg/kg p.o. in 20% 2-hydroxipropylcyclodextrin solution; n=4)) or vehicle (n=7) for 5 days significantly improved neurological function when treatment started 2 days after stroke in the rat, FIG. 3A.

Figure 3B:
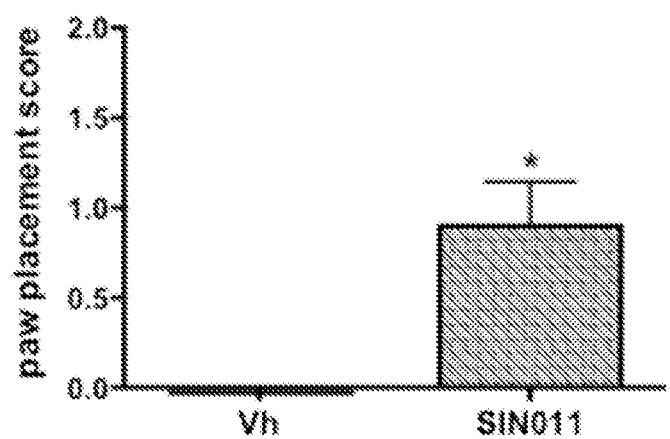
Figure 3C:
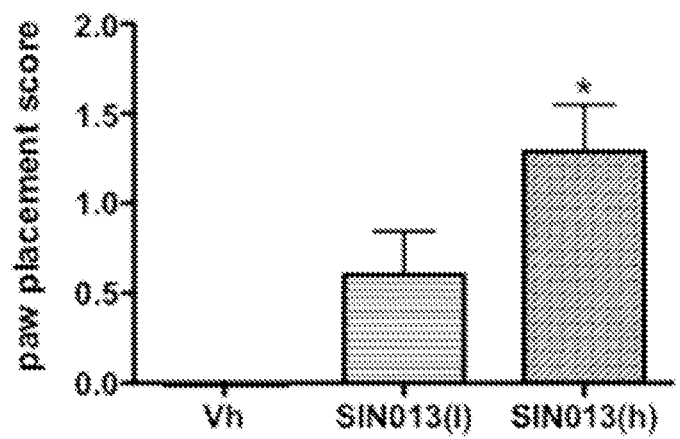
Figure 3D:
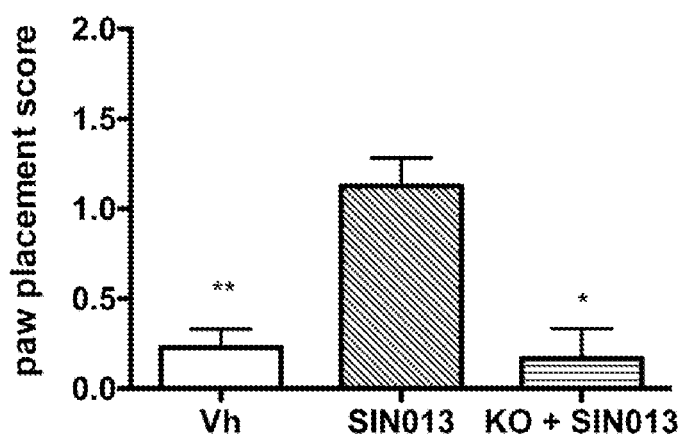
Figure 3E:
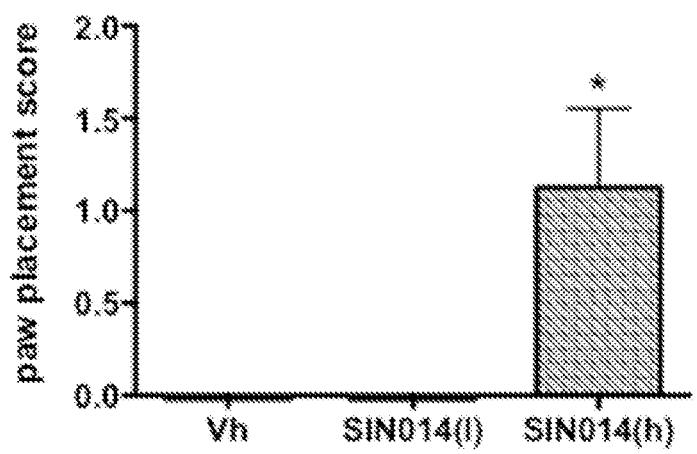
FIG. 3E: The effect of SIN014 [2,5-dimethyl-1-[4-fluoro-phenyl]imidazol-4-yl]ethynyl]pyridine, (RG7090, Basimglurant)) of functional recovery after stroke in the mouse.
Figure 3F:
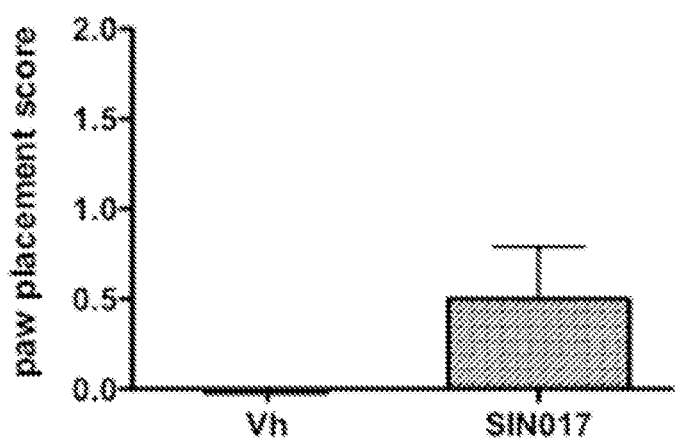
FIG. 3F: Effect of SIN017 (3-fluoro-5-(5-((2-methylthiazol-4-yl) ethynyl)pyridin-2-yl)benzonitrile, STX107) on functional recovery in the mouse.

The effect of daily administration of SIN 011 (mavoglurant) (30 mg/kg p.o.) or vehicle (0.5% HPMC) to mice, on paw placement function after stroke is shown in FIG. 3B. Treatment started 2 days after stroke and continued for 5 days. No recovery was seen in the vehicle group (n=5) while a significant recovery of paw function was seen in the treatment group (n=5) (p<0.01, Mann-Whitney).
FIG. 3C displays the effect of administration of SIN013 (CTEP) (2 mg/kg every 48 h (SIN013(1) (n=5) or 2 mg/kg daily SIN013(h) (n=7)) or vehicle (n=4). The treatments started 2 days after stroke and continued for 5 days. While no improvement of paw function was seen in the vehicle treated group, both treatment paradigms provide enhancement of function, which was significant in the 2 mg/kg daily dose regimen (p<0.05, Kruskal-Wallis). The enhancement of recovery after stroke by SIN013 in the mouse, FIG. 3C was confirmed in the rat model of stroke, FIG. 3D. Treatment with SIN013 (2 mg/kg/day p.o. in 0.3% Tween80 in saline, n=8) for 5 days significantly improved paw placement function compared to vehicle group (n=11). Treatment was initiated 2 days after stroke and continued for 5 days. In mGluR5 KO rats (n=3) the recovery stimulated by SIN013 treatment was not seen and the deficit was similar to that in the vehicle treated wild type rats. This confirm the evidence (FIG. 2D) that the stimulating effect of mGluR5 NAMs on recovery of lost brain function after stroke is mediated by the mGluR5 receptor.
Treatment of mice with SIN014 (basimglurant, RG7090; (1) 5 mg/kg p.o. and (h) 10 mg/kg p.o. in 0.3% Tween in saline) for 5 days improved functional recovery at the higher dose (10 mg/kg), FIG. 3E.
Daily treatment for 5 days with SIN017 (3 mg/kg in 0.5% HPMC, p.o. (n=3)) (STX107) also enhanced recovery of lost function in the mouse compared to the vehicle group (n=4), FIG. 3F. Treatment with SIN017 started 2 days after stroke.

Figure 2F:
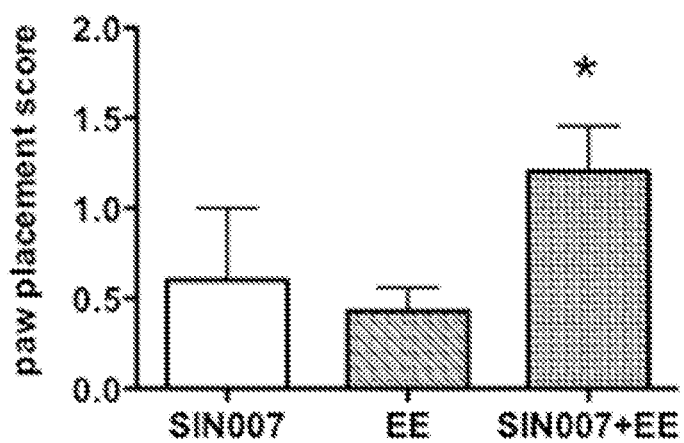
Figure 4A:
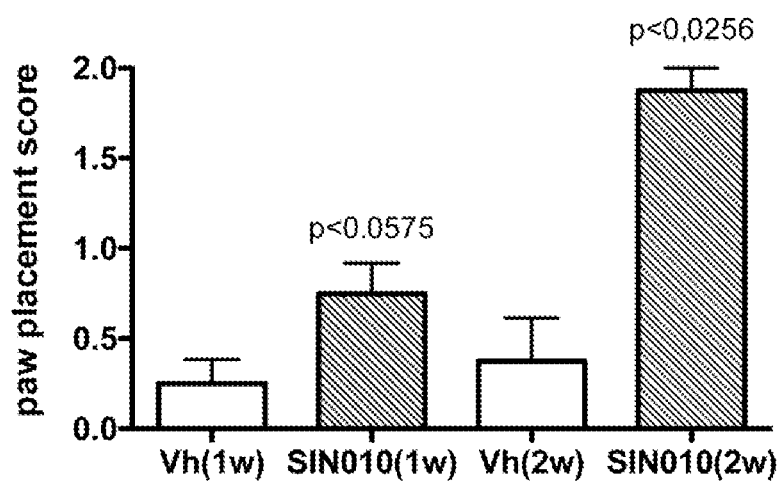
FIG. 4A: The effect of SIN 010 [1-(3-chlorophenyl)-3-(3-methyl-5-oxo-4H-imidazol-2-yl)urea, fenobam) on functional recovery in the rat at 1 week and 2 weeks after stroke.
Figure 4B:
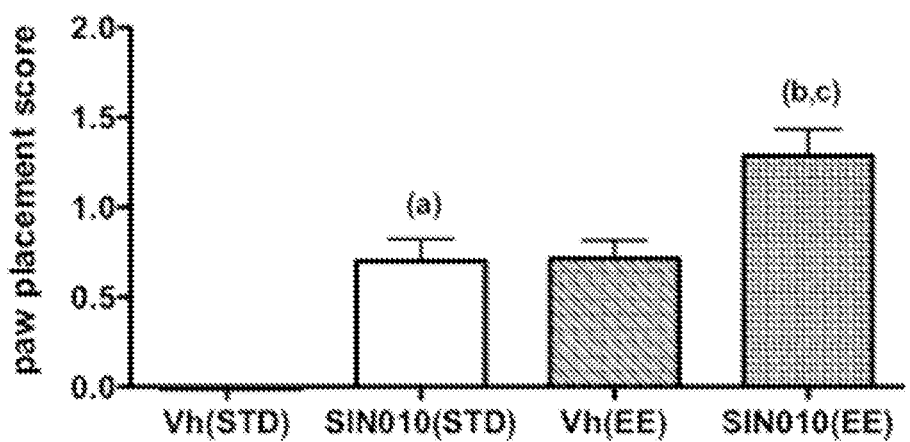
FIG. 4B: The additive effect of SIN010 treatment on the recovery enhancing effect of enriched housing in rats.
Figure 4C:
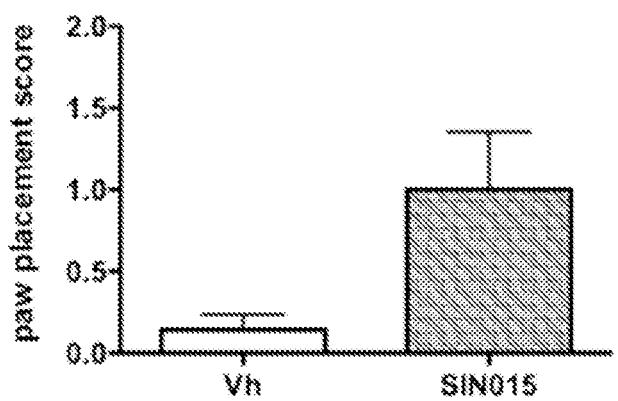
FIG. 4C: The effect of SIN 015 [3-fluoro-5-(3-(5-fluoropyridin-2-yl)-1,2,4-oxadiazol5-yl)benzonitrile] on functional recovery after stroke in the rat.

Example 4. The Effect of the Non-Alkyne mGluR5 NAMs, SIN010 and SIN015 on Functional Recovery after Stroke Experimental Procedure
Animals were as in Examples 1 and 2.
SIN 010 [1-(3-chlorophenyl)-3-(3-methyl-5-oxo-4H-imidazol-2-yl)urea, fenobam] and SIN015 [3-fluoro-5-(3-(5-fluoropyridin-2-yl)-1,2,4-oxadiazol5-yl)benzonitrile] were synthesized by Beijing Honghui Meditech Co., Ltd, (Beijing, China). All structures were confirmed by $H^1$—NMR and purity was >97%. SIN10 was suspended in 20% 2-hydroxicyclodextrin, and SIN015 in 0.5% HPMC. The compounds suspended in vehicle were sonicated for 15 minutes in order to obtain a stable suspension.
Administration of the compounds was made as in Example 3.
Induction of stroke, assessment of neurological function, perfusion of animals, immunostaining and assessment of infarct size were made as in Example 1.
Results
SIN010 (fenobam) given daily p.o. (10 mg/kg p.o, n=12) for 5 days (SIN010(1w), n=8) or for 12 days (SIN010(2w), n=4, (Vh, n=4) improves recovery function after stroke in the rat, FIG. 4A. Treatment was initiated at 2 days after stroke. A time dependent improvement of function was seen which was significant after 12 days of treatment compared to vehicle. A similar improvement if seen in mice subjected to stroke are treated with SIN010 starting two days after stroke, FIG. 4B. In addition, combining enriched housing (n=5) with daily treatment with SIN010 in mice 2 days after stroke further improves recovery compared to Vh (n=5), EE alone (n=7) or SIN010 (n=5) treatment alone, FIG. 4B. (a) denotes p<0.05 Vh vs SIN010 treatment, (b) SIN010 treatment+EE vs Vh, (c) SIN010 treatment+EE vs SIN010 alone. This result is similar to that found in the mouse treated with SIN007 in combination with enriched housing, FIG. 2F, strongly suggesting an additive effect of the combination treatment. SIN 015, 3-fluoro-5-(3-(5-fluoropyridin-2-yl)-1,2,4-oxadiazol5-yl)benzonitrile given in a dose of 3 mg/kg (n=4) for 5 days staring 2 days after stroke, improved recovery of function, FIG. 4C.

The invention claimed is:

1. Method of treating or alleviating mature brain damage, comprising administering a therapeutically effective amount of a negative allosteric modulator (NAM) of the metabotropic glutamate receptor 5 (mGluR5) to a patient having brain damage in which cell death subsided and which said damage does not progress further.

2. The method of claim 1, wherein the treatment results in improvement of recovery of brain function of a patient suffering from a mature brain damage.

3. The method of claim 1, wherein said NAM is selected from the group consisting of:

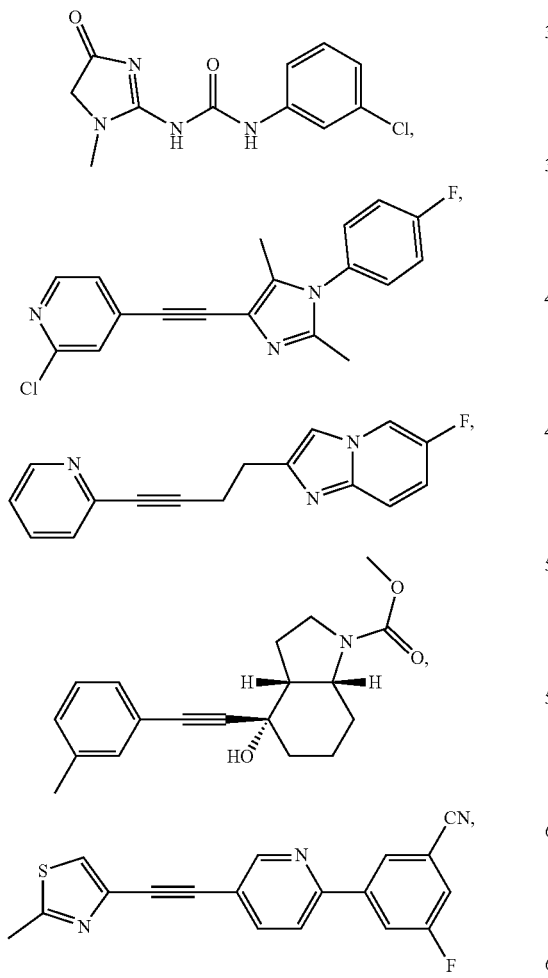

-continued

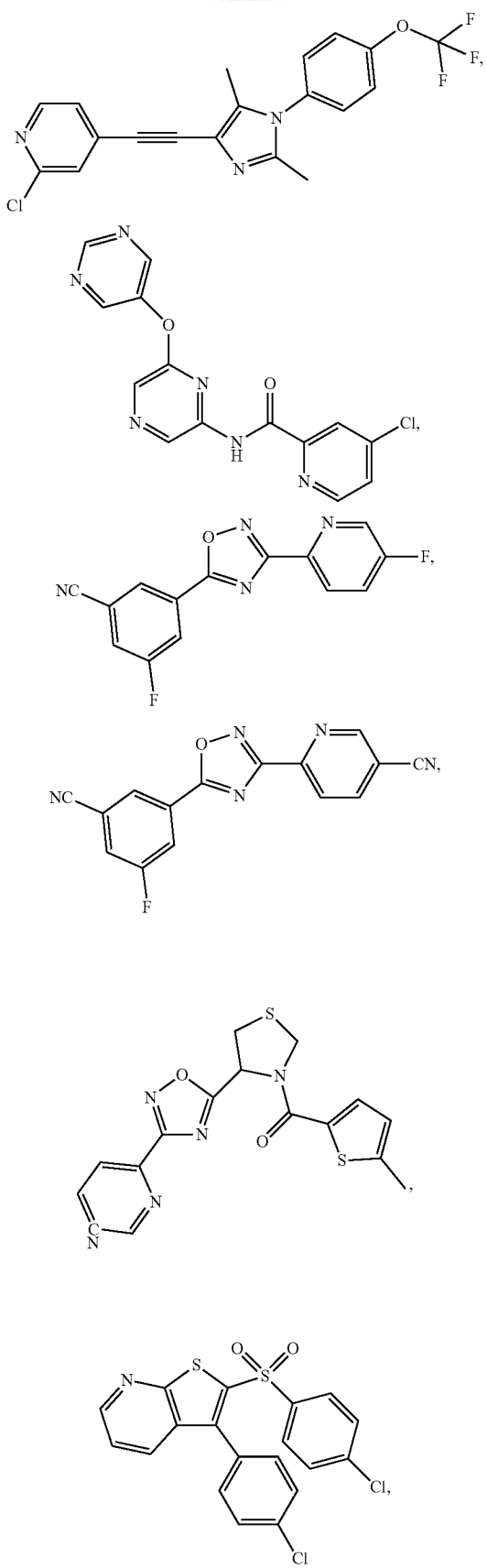

-continued
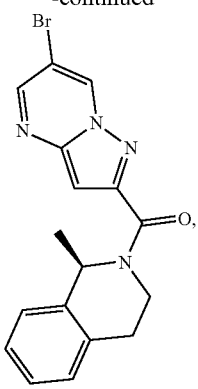
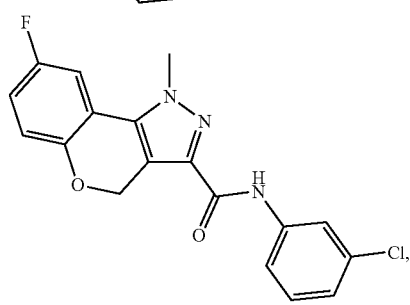
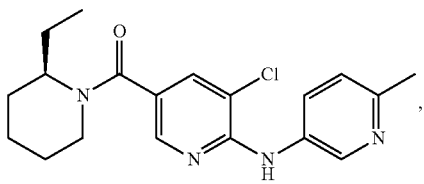
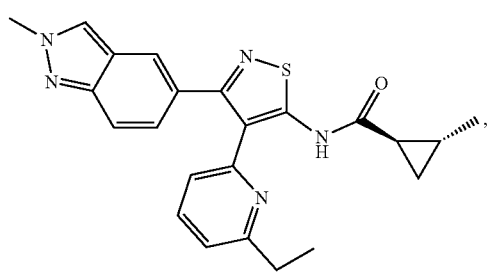
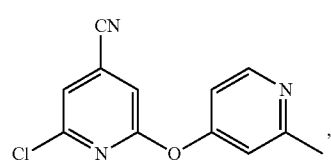
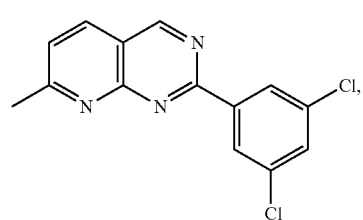
-continued
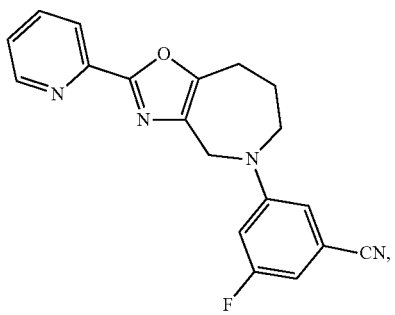
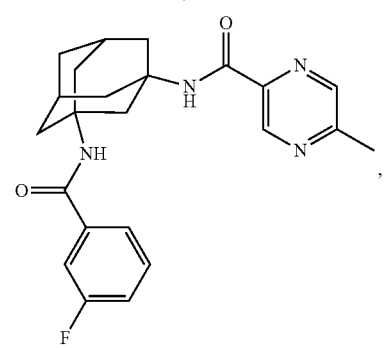
and pharmaceutically acceptable salts and solvates thereof.
4. The method of claim 1, wherein said NAM is selected from the group consisting of:
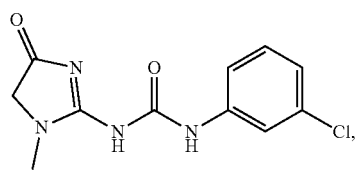
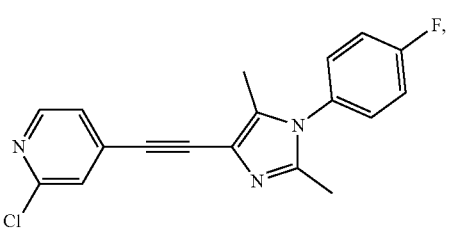

-continued

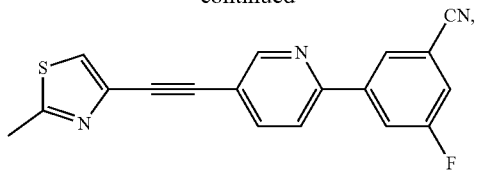

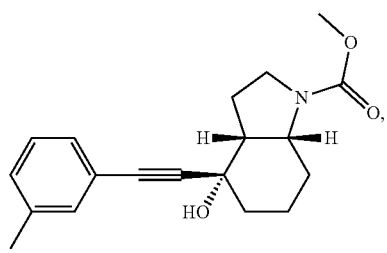 [SMILES: COC(=O)N1CC[C@@H]2[C@H]1CCC[C@@]2(O)C#Cc1cccc(C)c1]

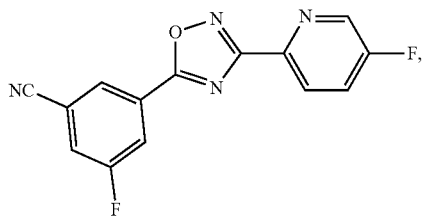 [SMILES: N#Cc1cc(F)cc(-c2nc(-c3ccc(F)cn3)no2)c1]

and pharmaceutically acceptable salts and solvates thereof.

5. The method of claim 1, wherein said NAM is

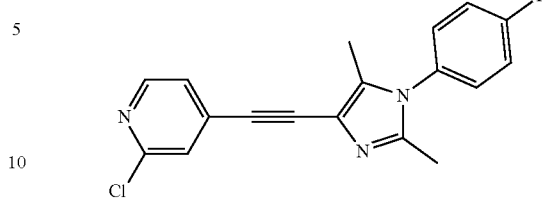

and pharmaceutically acceptable salts and solvates thereof.

6. The method of claim 1, wherein said mature brain damage has been caused by a condition selected from the group consisting of stroke, brain trauma, cardiopulmonary arrest and acute brain injury.

7. The method of claim 6, wherein said brain damage has been caused by stroke which has resulted in a post-stroke disorder selected from the group consisting of cognitive impairment, depression, fatigue and sensori- and motor dysfunction.

8. The method of claim 1, wherein said treatment is to be initiated once a neuroprotective treatment is no longer effective.

9. The method of claim 8, wherein said treatment is to be initiated after neuroprotective treatment has been finalized.

10. The method of claim 1, wherein said treatment is to be initiated not earlier than 6 hours after the initial acute brain damage has occurred.

11. The method of claim 1, wherein the treatment is combined with transcranial magnetic stimulation, electrical stimulation and/or physical and behavioral therapies.

* * * * *